(12) United States Patent
Loibner et al.

(10) Patent No.: US 9,757,433 B2
(45) Date of Patent: Sep. 12, 2017

(54) MODIFIED ACE2 POLYPEPTIDES

(71) Applicant: Apeiron Biologicals AG, Vienna (AT)

(72) Inventors: Hans Loibner, Vienna (AT); Bernhard Peball, Vienna (AT); Manfred Schuster, Vienna (AT); Stefan Stranner, Vienna (AT)

(73) Assignee: Apeiron Biologicals AG (AT)

( * ) Notice: Subject to any disclaimer, the term of this patent is extended or adjusted under 35 U.S.C. 154(b) by 26 days.

(21) Appl. No.: 14/760,529

(22) PCT Filed: Jan. 13, 2014

(86) PCT No.: PCT/EP2014/050457
§ 371 (c)(1),
(2) Date: Jul. 13, 2015

(87) PCT Pub. No.: WO2014/108530
PCT Pub. Date: Jul. 17, 2014

(65) Prior Publication Data
US 2015/0353910 A1    Dec. 10, 2015

Related U.S. Application Data

(60) Provisional application No. 61/752,023, filed on Jan. 14, 2013.

(51) Int. Cl.
*A61K 38/00* (2006.01)
*A61K 38/48* (2006.01)
*C12N 9/48* (2006.01)

(52) U.S. Cl.
CPC .......... *A61K 38/4813* (2013.01); *C12N 9/485* (2013.01); *A61K 38/00* (2013.01); *C12Y 304/17023* (2013.01)

(58) Field of Classification Search
CPC ................ A61K 38/4813; C12N 9/485; C12Y 304/17023
See application file for complete search history.

(56) References Cited

U.S. PATENT DOCUMENTS 8,586,319 B2 * 11/2013 Schuster .................. C12N 9/64
424/94.63
2007/0275095 A1    11/2007 Kossor

FOREIGN PATENT DOCUMENTS

| AT | 505 262 A1 | 12/2008 |
|---|---|---|
| WO | WO 2008/046125 A1 | 4/2008 |
| WO | WO 2008/151347 A1 | 12/2008 |
| WO | WO 2013/119870 A1 | 8/2013 |

OTHER PUBLICATIONS

Tipnis et al. 2000; A human homolog of angiotensin-converting enzyme. Journal of Biological Chemistry. 275(43):33238-33243.*
Bunning et al. 1985; The functional role of zinc in angiotensin converting enzyme: implications for the enzyme metabolism. Journal of Inorganic Biochemistry. 24(3): 183-198, only p. 183 provided.*
Carvalho et al. 1996; Electron paramagnetic resonance studies of cobalt-substituted angiotensin I-converting enzyme. Journal of Inorganic Biochemistry. 62: 147-153.*
Nikhil H Gokhale, et al., "metal lopeptide-promoted inactivation of angiotensin-converting enzyme and endothelin-converting enzyme 1: toward dual-action therapeutics", Journal of Biological Inorganic Chemistry, springer, berlin, de, vol. 11, No. 7, Jul. 28, 2006 (Jul. 28, 2006), pp. 937-947.
Nobuko Sarukura et al., "Effects of dietary zinc deprivation on zinc concentration and ratio of apo/holo-activities of angiotensin converting enzyme in serum of mice", Auris Nasus Larynx, vol. 39, No. 3, Jun. 1, 2012 (Jun. 1, 2012), pp. 294-297.
T. Tamura, et al., "In vitro zinc stimulation of angiotensin-converting enzyme activities in various tissues of zinc-deficient rats", Nutrition Research, vol. 14, No. 6, Jun. 1, 1994 (Jun. 1, 1994), pp. 919-928.

* cited by examiner

*Primary Examiner* — Karen Cochrane Carlson
(74) *Attorney, Agent, or Firm* — William T. Han; Edward R. Gimmi (57) ABSTRACT

The present invention relates to modified angiotensin converting enzyme 2 (ACE2) polypeptides and pharmaceutical and analytical uses thereof. In particular, the present invention relates to $Zn^{2+}$ depleted-, $Zn^{2+}$ free-, mixed metal- and metal ion substituted-ACE2 as well as methods for the manufacture of these variants and uses thereof, such as therapeutic and analytic uses of these ACE2 variants.

11 Claims, 4 Drawing Sheets

Figure 5: SEQ ID No:1

MSSSS WLLLS LVAVT AA

QSTIE EQAKT FLDKF NHEAE DLFYQ SSLAS WNYNT NITEE NVQNM NNAGD KWSAF LKEQS TLAQM YPLQE IQNLT VKLQL QALQQ NGSSV LSEDK SKRLN TILNT MSTIY STGKV CNPDN PQECL LLEPG LNEIM ANSLD YNERL WAWES WRSEV GKQLR PLYEE YVVLK NEMAR ANHYE DYGDY WRGDY EVNGV DGYDY SRGQL IEDVE HTFEE IKPLY EHLHA YVRAK LMNAY PSYIS PIGCL PAHLL GDMWG RFWTN LYSLT VPFGQ KPNID VTDAM VDQAW DAQRI FKEAE KFFVS VGLPN MTQGF WENSM LTDPG NVQKA VCHPT AWDLG KGDFR ILMCT KVTMD DFLTA HHEMG HIQYD MAYAA QPFLL RNGAN EGFHE AVGEI MSLSA ATPKH LKSIG LLSPD FQEDN ETEIN FLLKQ ALTIV GTLPF TYMLE KWRWM VFKGE IPKDQ WMKKW WEMKR EIVGV VEPVP HDETY CDPAS LFHVS NDYSF IRYYT RTLYQ FQFQE ALCQA AKHEG PLHKC DISNS TEAGQ KLFNM LRLGK SEPWT LALEN VVGAK NMNVR PLLNY FEPLF TWLKD QNKNS FVGWS TDWSP YADQS IKVRI SLKSA LGDKA YEWND NEMYL FRSSV AYAMR QYFLK VKNQM ILFGE EDVRV ANLKP RISFN FFVTA PKNVS DIIPR TEVEK AIRMS RSRIN DAFRL NDNSL EFLGI QPTLG PPNQP PVSIW LIVFG VVMGV IVVGI VILIF TGIRD RKKKN KARSG ENPYA SIDIS KGENN PGFQN TDDVQ TSF

MODIFIED ACE2 POLYPEPTIDES

This application is a 371 of International Application No. PCT/EP2014/050457, filed 13 Jan. 2014, which claims the benefit of U.S. Provisional Application No. 61/752,023, filed 14 Jan. 2013, which are incorporated herein in their entirety.

FIELD OF THE INVENTION

The present invention relates to modified angiotensin converting enzyme 2 (ACE2) variants and pharmaceutical and analytical uses thereof. In particular, the present invention relates to $Zn^{2+}$ depleted-, $Zn^{2+}$ free-, mixed metal- and metal ion substituted-ACE2 as well as methods for the manufacture of these variants and uses thereof, such as therapeutic and analytic uses of these ACE2 variants.

BACKGROUND TO INVENTION

ACE2 (angiotensin converting enzyme 2, also known as angiotensin-converting enzyme-related carboxypeptidase; Enzyme Commission Number: 3.4.17.23) is a key metalloprotease of the Renin Angiotensin System (RAS), see Donoghue et al., Circ. Res. 87, 2002: e1-e9; Tipnis et al., J. Biol. Chem., 275(43), 2000, 33238-43). ACE2 was initially identified as an ACE analogue. Tipnis et al. describe the isolation of ACE2 (in that case still referred to as ACEH) from CHO cells and its cDNA isolation.

Both ACE and ACE2 are metalloproteases with a catalytic zinc atom in the centre. ACE and ACE2 were subsequently discovered to be different in terms of activity as well as mechanism. ACE increases blood pressure, whereas ACE2 decreases blood pressure. Mechanistically, ACE is a peptidyl dipeptidase, whereas ACE2 is a carboxypeptidase (Towler et al., J. Biol Chem 279, 2004, 17996-18007).

ACE2 primarily exists as a membrane anchored zinc metalloprotease, which acts in the blood circulation and induces local effects in affected organs, as well as systemic effects via the blood circulation. ACE2 is expressed in the vascular system as well as in most organs, but predominantly in the kidneys, liver, heart, lungs and testes. It cleaves, as a monopeptidase, thereby activating or inactivating a plethora of substrates, including peptides of the RAS such as angiotensin II (Ang II), which is cleaved to angiotensin 1-7 (Ang1-7), and angiotensin I (Ang I), which is cleaved to angiotensin 1-9 (Ang1-9), as well as Apelin, Pro-Dynorphin, Des-Arg-Bradykinin, and others (Vickers, C. et al., J. Biol. Chem., 277, 2002, 14838-14843). ACE2 plays a central role within the RAS as a counter-regulator to the ACE-Ang II-$AT_1$ receptor axis. ACE2 acts by shifting from the pro-inflammatory, hypertensive, proliferative and vasoconstrictive axis, which is mediated by Angiotensin II, to the counter-regulatory axis triggered by the cleavage of Ang II by ACE2 to generate Ang 1-7 (Danilczyk, U. & Penninger, Circ. Res., 98, 2006, 463-471; Vickers, C. et al., J. Biol. Chem., 277, 2002, 14838-14843), and to a lesser extent, the cleavage of Ang I by ACE2 to generate Ang 1-9. ACE2 is considered to be an important modulator of homeostasis (Ferrario, C. M., et al., J. Am. Soc. Nephrol., 9, 1998, 1716-1722). The catalytic activity of ACE2 is approximately 400-fold higher with AngII than with AngI (Vickers, C. et al., J. Biol. Chem., 277, 2002, 14838-14843). A soluble form of ACE2 is also found in the circulation, which lacks the transmembrane domain. It is this soluble form that is better suited to being used as an active compound in a wide array of therapeutic approaches than the membrane-bound form.

Soluble and recombinant forms of ACE2 have been developed to treat life-threatening diseases such as acute pulmonary and cardiac conditions, as well as fibrotic and oncologic diseases.

The function of ACE2 as an ACE counter-regulator was first reported in the international patent application, publication number WO2004/000367. The application discloses therapeutic treatments of various diseases, such as hypertension, congestive heart failure, chronic heart failure, acute heart failure, myocardial infarction, arteriosclerosis and renal failure and lung disease, including Adult Respiratory Distress Syndrome (ARDS).

International patent application, publication number WO2004/023270 describes the crystallization of ACE2.

International patent application, publication number WO2008/151347 and US patent application, publication number US2010/310546 describe ACE2 glycosylation and ACE2 dimers.

Methods to determine ACE2 activity are e.g. described in the international patent application, publication number WO 2008/046125 A and US patent application, publication number US 2010/0261214.

International patent application, publication number WO2009/086572 describes the use of ACE2 in the treatment of liver disease, in particular inflammatory liver diseases, and fibrosis.

International patent application, publication number WO2009/076694 describes immune therapies with ACE2.

International patent application, publication number WO2009/124330 describes the treatment of various tumours with ACE2.

ACE2 is described as a zinc containing metalloprotease, a so-called zinc-protease. The current fully active formulations for clinical use contain an equimolar zinc/protein ratio. Zinc is thereby complexed in the active centre of the enzyme. The drug product formulation is usually supplemented with $ZnCl_2$ to stabilize enzymatic activity by inhibiting loss of enzyme-bound zinc.

BRIEF DESCRIPTION OF THE INVENTION

According to a first embodiment, there is provided a population of angiotensin converting enzyme 2 (ACE2) polypeptides having depleted levels of $Zn^{2+}$ in the active sites.

According to a first aspect of the invention, there is provided a population of ACE2 polypeptides, wherein the active sites are substantially free of any metal ion.

According to a second aspect of the invention, there is provided a population of ACE2 polypeptides, wherein the active sites are occupied by a transition metal ion, or a post-transition metal ion selected from $Co^{2+}$, $Ni^{2+}$, $Mn^{2+}$, $Cu^{2+}$, $Zn^{2+}$, $Fe^{3+}$, $Fe^{2+}$, $Pb^{2+}$ Al, Ga, In, Sn, Tl, Pb, Bi and Po, preferably $Co^{2+}$, $Zn^{2+}$, $Ni^{2+}$, $Pb^{2+}$ $Al^{3+}$, $Al^{2+}$ and $Sn^{2+}$, e.g. $Zn^{2+}$, $Fe^{3+}$, $Cu^{2+}$, $Mn^{2+}$ and $Al^{3+}$.

According to a third aspect of the invention, there is provided a population of ACE2 polypeptides, wherein the active sites which are not occupied by zinc, are occupied by one or more transition metal ions or post-transition metal ions selected from $Co^{2+}$, $Ni^{2+}$, $Mn^{2+}$, $Cu^{2+}$, $Zn^{2+}$, $Fe^{3+}$, $Fe^{2+}$, $Pb^{2+}$ Al, Ga, In, Sn, Tl, Pb, Bi and Po, preferably $Co^{2+}$, $Zn^{2+}$, $Ni^{2+}$, $Pb^{2+}$, $Al^{3+}$, $Al^{2+}$ and $Sn^{2+}$, e.g. $Zn^{2+}$, $Fe^{3+}$, $Cu^{2+}$, $Mn^{2+}$ and $Al^{3+}$.

According to a second embodiment, there is provided the use of a population of ACE2 polypeptides to cleave an ACE2 substrate in a solution.

According to a third embodiment, there is provided a method for the preparation of a population of ACE2 polypeptides, comprising the steps of:
a. Expressing the ACE2 polypeptides in a cell system;
b. Isolating the expressed polypeptides;
c. Removing some or all of the metal ions bound in the active site by the addition of a metal-chelating agent.

According to a fourth embodiment, there is provided a pharmaceutical composition comprising a population of ACE2 polypeptides and a pharmaceutically acceptable carrier or excipient.

According to a fifth embodiment, there is provided a population of ACE2 polypeptides for use in therapy.

According to a sixth embodiment, there is provided a population of ACE2 polypeptides for use in the treatment or prevention of a disease selected from hypertension (including high blood pressure), congestive heart failure, chronic heart failure, acute heart failure, contractile heart failure, myocardial infarction, arteriosclerosis, kidney failure, renal failure and lung disease, such as Adult Respiratory Distress Syndrome (ARDS), Acute Lung Injury (ALI), chronic obstructive pulmonary disease (COPD), pulmonary hypertension, renal fibrosis, chronic renal failure, acute renal failure, chronic renal failure, acute kidney injury and multi-organ dysfunction syndrome.

According to a sixth embodiment, there is provided the use of a population of ACE2 polypeptides in the manufacture of a medicament for the treatment or prevention of a disease selected from hypertension (including high blood pressure), congestive heart failure, chronic heart failure, acute heart failure, contractile heart failure, myocardial infarction, arteriosclerosis, kidney failure, renal failure and lung disease, such as Adult Respiratory Distress Syndrome (ARDS), Acute Lung Injury (ALI), chronic obstructive pulmonary disease (COPD), pulmonary hypertension, renal fibrosis, chronic renal failure, acute renal failure, chronic renal failure, acute kidney injury and multi-organ dysfunction syndrome.

According to a seventh embodiment, there is provided a method of treating or preventing a disease selected from hypertension (including high blood pressure), congestive heart failure, chronic heart failure, acute heart failure, contractile heart failure, myocardial infarction, arteriosclerosis, kidney failure, renal failure and lung disease, such as Adult Respiratory Distress Syndrome (ARDS), Acute Lung Injury (ALI), chronic obstructive pulmonary disease (COPD), pulmonary hypertension, renal fibrosis, chronic renal failure, acute renal failure, chronic renal failure, acute kidney injury and multi-organ dysfunction syndrome comprising administering to a patient in need thereof an effective amount of a population of ACE2 polypeptides.

DETAILED DESCRIPTION OF THE INVENTION

It has been discovered that zinc is not an absolute requirement for ACE2 structure and activity. In addition, zinc can be replaced by other metal ions while retaining enzymatic activity. Therefore, the present invention provides for further variants of ACE2 polypeptides, in particular ACE2 polypeptides having depleted levels of zinc in the active site, or wherein the active site is substantially free of zinc (or any other metal ion), ACE2 polypeptides wherein the active site is occupied by another metal ion, other than zinc, and a population of ACE2 polypeptides having a mixture of zinc and another metal ion in the active sites.

"$Zn^{2+}$ depleted ACE2 (polypeptides)" also referred to as "zinc depleted ACE2 (polypeptides)" or "ACE2 (polypeptides) having depleted levels of $Zn^{2+}$ (or zinc) in the active site" are terms which are used interchangeably throughout. Such zinc-depleted ACE2 is characterized by a lack of, or reduced levels of zinc, especially a $Zn^{2+}$ ion, in the zinc-binding site of ACE2. The zinc-binding site is alternatively referred to as the "active site" herein. When the ACE2 polypeptide is in dimeric form, an example of a zinc-depleted dimer is such that at least one of the ACE2 monomers within the dimer is lacking a zinc atom in the active site (i.e. in the zinc-binding site) of the monomer. The term also refers to a population of ACE2 polypeptides, wherein the zinc:ACE2 molar stoichiometry is less than 1:1. One skilled in the art will readily appreciate when a statement herein is able to refer to the polypeptide in individualised form and when said statement necessarily refers to a population of polypeptides.

In one embodiment, there is provided a zinc-depleted ACE2 polypeptide which is a metal ion-free ACE2 polypeptide. As used herein "Zinc-free ACE2 (polypeptides)" and "metal ion-free ACE2 (polypeptides)" are used interchangeably. Such a metal ion-free ACE2 polypeptide has substantially no zinc or other metal ion present in the active site. In one embodiment, the metal ion-free ACE2 polypeptide has no detectable levels of zinc or other metal ions in the active site.

In another embodiment, there is provided a zinc-depleted ACE2 polypeptide which is a metal-substituted ACE2 polypeptide. As used herein "metal-substituted ACE2 (polypeptides)" refers to an ACE2 polypeptide or a population of ACE2 polypeptides wherein the active site(s) is occupied by one or more transition metal ion or post-transition metal ion other than the native $Zn^{2+}$ ion.

In another embodiment, there is provided a zinc-depleted ACE2 polypeptide which is a mixed-metal ACE2 polypeptide. As used herein, "mixed-metal ACE2 (polypeptides)" are used to describe a population of ACE2 polypeptides wherein a proportion of the naturally-bound zinc in the active site has been removed and replaced with another transition metal ion or post-transition metal ion. In a population of mixed-metal ACE2 polypeptides therefore, a sub-equimolar amount of zinc to polypeptide will be present in the active sites, as well as a further proportion of transition metal ions or post-transition metal ions in other active sites. It will clearly be appreciated that it is not possible for more than one individual metal ion to occupy a single active site at any one time, therefore in a mixed metal ACE2 polypeptide, the occupancy of the active site is assessed across the population.

"Population" as used herein refers to more than one polypeptide, wherein the characteristics of that population are taken as an average. In particular, it is used herein to refer to populations of ACE2 polypeptides for example having a particular ratio of empty active sites as compared to active sites which are occupied, for example by a transition metal ion. Within the population, individual ACE2 polypeptides may only have occupied or empty active sites, but over the whole population, the given ratios are achieved.

"Free zinc" or "free metal ion(s)" are to be understood as zinc, or another metal ion accordingly, being free and therefore available to enter the zinc binding site(s) of the ACE2 polypeptide, e.g. a metal ion or zinc ion which is not complexed by other components, such as chelators, in a preparation or composition.

"Poor metal (element/ion)" and "post-transition metal (element/ion)" are used interchangeably in the present application. It is to be understood that this term encompasses the following metal ions: aluminium (Al), gallium (Ga), indium (In), tin (Sn), thallium (Tl), lead (Pb), bismuth (Bi) and polonium (Po). Preferably, the post-transition metal is selected from aluminium and tin, e.g. $Al^{2+}$, $Al^{3+}$ and $Sn^{2+}$. The term is intended to cover the post-transition metals in all possible positively charged oxidation states, preferably ions in the 2+ or 3+ oxidation state, but most particularly in the 2+ oxidation state.

"Transition metal (element/ion)" refers to those elements of groups 3 to 12, and in periods 4, 5, 6 and 7 of the periodic table, including, but not limited to chromium (Cr), cobalt (Co), nickle (Ni), manganese (Mn), copper (Cu), iron (Fe), zinc (Zn), molybdenum (Mo), ruthenium (Ru), rhodium (Rh), palladium (Pd), silver (Ag) and cadmium (Cd). The term is intended to cover the transition metals in all possible positively charged oxidation states, preferably ions in the 2+ or 3+ oxidation state. In one embodiment, the transition metal element is a period 4 or 5 element of groups 3 to 12 of the periodic table. In another embodiment, the transition metal is selected from $Co^{2+}$, $Ni^{2+}$, $Mn^{2+}$, $Cu^{2+}$, $Fe^{3+}$, $Fe^{2+}$ and $Pb^{2+}$. In a further embodiment, the transition metal is selected from $Co^{2+}$, $Ni^{2+}$ and $Pb^{2+}$. In a further embodiment, the metal ion is selected from $Fe^{3+}$, $Cu^{2+}$, and $Mn^{2+}$. In a further embodiment, the transition metal is selected from $Co^{2+}$ and $Ni^{2+}$. In another embodiment, the transition metal is selected from $Fe^{3+}$ and $Mn^{2+}$.

The human ACE2 polypeptide (UniProt sequence data base entry: Q9BYF1) comprises a signal peptide (amino acids 1 to 17), an extracellular domain (amino acids 18 to 740), a helical transmembrane domain (amino acids 741 to 761) and a cytoplasmic domain (amino acids 762 to 805).

The zinc-binding region of ACE2 contains a zinc-binding motif; HEXXH, which corresponds to amino acids 374 to 378 (in BOLD) of the full 805 amino acid long ACE2 sequence according to SEQ ID No. 1. The crystal structure of ACE2 is published for the native enzyme (PDB database entry: 1R42), and as inhibitor-bound enzyme (PBD database entry: 1R4L), illustrating the zinc ion in the $Zn^{2+}$ binding site.

According to the present invention, the ACE2 polypeptide may be a full-length ACE2 polypeptide or a fragment thereof. In one embodiment, the fragment comprises amino acids 374 to 378 of SEQ ID No: 1. In one embodiment, the ACE2 polypeptide comprises amino acids 1 to 740 of SEQ ID NO:1. In another embodiment, the ACE2 polypeptide is soluble ACE2 lacking a transmembrane domain and/or lacking the N-terminal signal peptide. In another embodiment of the invention, the ACE2 polypeptide comprises or consists of the amino acid sequence of the extracellular domain of ACE2. In another embodiment, the ACE2 polypeptide comprises or consists of amino acids 18 to 740, or of amino acids 18 to 615 of SEQ ID NO:1.

ACE2 polypeptides or ACE2 polypeptide fragments include human ACE2 or fragments thereof or any homologous orthologue thereof, with the same or similar native qualitative activity. Therefore, ACE2 originating from mouse, rat, hamster, swine, primates or cattle is also encompassed by the present invention. In one embodiment, the ACE2 polypeptide is of human origin. ACE2 is a universal enzyme in all mammals having the identical Ang II substrate. For therapeutic uses, the ACE2 polypeptide may therefore also be used in foreign organisms. Thus, for example, humans, mice, rats, hamsters, swine, primates or cattle can be treated with ACE2 according to the present invention, regardless of the source of the ACE2. Preferably, the therapeutic ACE2 polypeptide originates from the same organism that is to be treated, in order to minimize the risk of an immunogenic response, for example an ACE2 polypeptide of human origin for the treatment of a human patient.

ACE2 polypeptides of the present invention may optionally be glycosylated. The soluble domain of native human ACE2 has seven N-glycosylation sites. In one embodiment, 3, 4, 5, 6 or 7 of the possible N-glycosylation positions of the ACE2 polypeptides according to the invention, which correspond to Asn53, Asn90, Asn103, Asn322, Asn432, Asn546, Asn690 of SEQ ID NO: 1, are glycosylated and/or the ACE2 polypeptide has a sugar content of greater than 10% (percent by weight of the total ACE2 polypeptide) or 11%, 12%, 13%, 14%, 15%, 16%, 17%, 18%, 19%, in particular greater than 20%, 21%, 22%, 23%, 24%, or 25% by weight.

The ACE2 polypeptides may be in monomeric or dimeric form. When present as a dimer, one or two zinc ions may be depleted, absent and/or substituted with another metal ion.

Methods for producing ACE2 polypeptides are described in international patent application, publication number WO2008/151347, see Example 1 and pages 12 second full paragraph to page 13, end of second full paragraph, incorporated herein by reference.

It will be appreciated that, according to the present invention, the zinc-depleted ACE2 polypeptides, the metal ion-free ACE2 polypeptides, the metal-substituted ACE2 polypeptides and the mixed-metal ACE2 polypeptides may comprise any of the ACE2 polypeptides or fragments described above, in particular in terms of amino acid sequences, glycosylation patterns, origin, and dimeric/monomeric form.

In one embodiment, the ACE2 polypeptide is a dimeric human ACE2 polypeptide comprising amino acids 18 to 740 of SEQ ID No: 1, is glycosylated at one or more positions independently selected from the group consisting of Asn53, Asn90, Asn103, Asn322, Asn432, Asn546, Asn690 of SEQ ID NO: 1, and has a sugar content of greater than 20% by weight.

According to a first aspect of the invention, there is provided an ACE2 polypeptide having depleted levels of $Zn^{2+}$ in the active site. In one embodiment, the molar ratio of $Zn^{2+}$:ACE2 is ≤1:1, for example ≤0.99:1, ≤0.98:1, ≤0.95:1, ≤0.92:1 or ≤0.90:1.

According to a second aspect of the invention, the zinc-depleted ACE2 molecules are substantially free of zinc ($Zn^{2+}$). However small impurities may remain and are encompassed by the present invention. In another embodiment, the molar ratio of $Zn^{2+}$:ACE2 is ≤0.50:1, ≤45:1, ≤0.40:1, ≤0.35:1, ≤0.30:1, ≤0.25:1, ≤0.20:1, ≤0.15:1, ≤0.10:1, ≤0.05:1, ≤0.02:1, or ≤0.01:1. The $Zn^{2+}$:ACE2 ratio refers to zinc found in the zinc binding site of ACE2. This may be measured, for example, by native purification of the polypeptide or by dialysis, then subjecting the resulting solid material to ICP-MS analysis. In one method, the zinc depleted ACE2 may be captured by binding to anti-ACE2-antibody coated beads, the eluted with a zinc-free eluant, then subjected to ICP-MS analysis. Using these methods, it can be determined that the resulting ratio of zinc to ACE2 polypeptide is due to the complexing of the zinc to the polypeptide in the active site.

In order to keep $Zn^{2+}$ from migrating to the binding site, a preparation or composition comprising a population of zinc-depleted ACE2 polypeptides of the invention also comprises little (according to the above ratios) or no free zinc. Free zinc levels (as well as zinc bound to the active site of ACE2) may be reduced in a particular preparation or composition by the addition of chelators such as EDTA, EGTA, 8-hydroxyquinoline, phenanthroline and/or dimercaprol (also called British-anti-Lewisite or BAL). The particular excess of chelating agent required is readily determined by one skilled in the art, and will depend on, amongst other things, the nature of the chelating agent employed, the pH value, and the type of metal ion to be removed. For removal of the native zinc from the active site, an excess in the region of 1000-fold of EDTA is appropriate (see Example 2 below).

Therefore, in a preparation or composition comprising a population of zinc-depleted ACE2 polypeptides, the above $Zn^{2+}$:ACE2 ratios refer to the amount of zinc in the ACE2 binding site. In a further embodiment, the amount of zinc ions in the preparation is reduced by the addition of metal-chelating agents. The amounts of such chelators may be as described below.

The present invention also provides methods of producing $Zn^{2+}$ depleted ACE2 polypeptides, comprising the steps of expressing the ACE2 polypeptide(s) in a cell, isolating the ACE2 polypeptide(s), and removing $Zn^{2+}$ from said ACE2 polypeptide(s), preferably with a metal-chelating agent. The ACE2 polypeptide(s) may be expressed in the presence or absence of zinc. However, in most cellular systems, zinc ions may be present and therefore the expressed ACE2 polypeptides usually contain zinc in the active site. This bound zinc may subsequently be removed e.g. by using a metal-chelating agent, such as EDTA, EGTA, 8-hydroxyquinoline, phenanthroline and/or dimercaprol, or by using ion-exchange chromatography. In another embodiment, the metal-chelating agent is used in excess, e.g. in concentrations of at least 2 times, 5 times, 10 times, 25 times, 50 times, 75 times, 100 times, 200 times, 300 times, 400 times, 500 times, 600 times, 700 times, 800 times, 900 times, 1000 times the total concentration of zinc in the preparation or composition, i.e. the zinc concentration in the solution and in the active site.

According to a third aspect of the present invention, the active site(s) of the ACE2 polypeptides are substantially free of any metal-ion, including zinc. However small impurities may remain and are encompassed by the present invention. In another embodiment, the molar ratio of metal ions:ACE2 is ≤0.50:1, ≤0.45:1, ≤0.40:1, ≤0.35:1, ≤0.30:1, ≤0.25:1, ≤20:1, ≤0.15:1, ≤0.10:1, ≤0.05:1, ≤0.02:1, or ≤0.01:1. The metal ion:ACE2 ratio refers to metal ions found in the active site of ACE2. This may be measured, for example, by native purification of the polypeptide or by dialysis, then subjecting the resulting solid material to ICP-MS analysis. In one method, the metal ion-free ACE2 may be captured by binding to anti-ACE2-antibody coated beads, then eluted with a metal ion-free eluant, then subjected to ICP-MS analysis. Using these methods, it can be determined that the resulting ratio of metal ions to ACE2 polypeptide is due to the complexing of the metal ions to the polypeptide in the active site.

Metal ion-free ACE2 polypeptides are enzymatically inactive, but structurally stable. They do not aggregate or disintegrate and can be reconstituted into active ACE2 by providing suitable metal ions. The high stability of the polypeptides may have benefits during storage with a long shelf-life, even during poor storage conditions, such as by interrupted cooling periods (e.g. during transit). Without being limited to theory, it may be that long-term stability may be improved due to the lack of activity, which may prevent autoproteolysis and/or may reduce zinc-mediated oxidation of the active site by acting as a Lewis acid. Moreover, with the ACE2 polypeptides according to the present invention, it is possible to regulate or fine-tune the ACE2 activity or bioavailability by metal depletion or substitution.

The zinc-depleted, zinc-free and metal ion-free ACE2 polypeptides of the present invention may be used as peptidases to cleave an ACE2 substrate in a solution comprising a metal ion. Alternatively, there is provided a method of cleaving an ACE2 substrate comprising contacting said ACE2 substrate with a zinc-depleted, zinc-free and/or metal ion-free ACE2 polypeptide(s) in a solution comprising a metal ion. In the solution comprising a metal ion, the zinc-depleted, zinc-free and/or metal ion-free ACE2 polypeptides will take up the free metal ion, chelate it in the active site and thereby reconstitute to a metal-substituted ACE2 polypeptide, such as a zinc-reconstituted ACE2, and regain its catalytic activity.

In such metal-comprising solutions, the metal ion is selected from a transition metal element or a post-transition metal element of the periodic table of elements. The metal ion is, in one embodiment, positively charged, in particular 2+ or 3+. Any such metal may occupy the zinc binding site of ACE2 to retain the activity of the ACE2. Zinc may also be replaced by other metal ions in order to restore the activity of the ACE2. Transition elements of the periodic table of elements are of groups 3 to 12 in periods 4, 5, 6 and 7, including Cr, Co, Ni, Mn, Cu, Fe, Zn, Mo, Ru, Rh, Pd, Ag and Cd, for example $Co^{2+}$, $Ni^{2+}$, $Mn^{2+}$, $Cu^{2+}$, $Fe^{3+}$, $Fe^{2+}$ and $Pb^{2+}$. In other embodiments, the transition element is a period 4 or 5 element. In a further embodiment, the transition metal is selected from $Co^{2+}$, $Ni^{2+}$ and $Pb^{2+}$. In a further embodiment, the metal ion is selected from $Fe^{3+}$, $Cu^{2+}$, and $Mn^{2+}$. In a further embodiment, the transition metal is selected from $Co^{2+}$ and $Ni^{2+}$. In another embodiment, the transition metal is selected from $Fe^{3+}$ and $Mn^{2+}$. Post-transition metals, also referred to as poor metals, are selected from Al, Ga, In, Sn, Tl, Pb, Bi and Po, e.g. $Al^{2+}$, $Al^{3+}$ and $Sn^{2+}$. In one embodiment, the post-transition metal is selected from aluminium and tin, e.g.

Examples of ACE2 substrates include, but are not limited to, Apelin, Pro-Dynorphin, Des-Arg-Bradykinin, bradykinin, angiotensin I (Ang I, which is cleaved to angiotensin 1-9 [Ang1-9]), angiotensin II (Ang II, which is cleaved to angiotensin 1-7 [Ang1-7]) and others. Furthermore, a number of artificial substrates exists, such as those described in US2010/0261214 (see paragraph [0032], on page 3, incorporated herein by reference), e.g. Mca-Ala-Pro-Lys(Dnp)-OH (Mca: (7-methoxy coumarin-4-yl)acetyl). Artificial substrates may be labelled, e.g. comprise both a fluorophore and a quencher, such that upon cleavage an optical signal is generate. The methods and uses of zinc-depleted, zinc-free and/or metal ion-free ACE2 polypeptides to cleave ACE2 substrates may further comprise the step of detecting cleavage products.

The methods and uses of zinc-depleted, zinc-free and/or metal ion-free ACE2 polypeptides to cleave ACE2 substrates may be performed in vivo, for example for therapeutic uses or to achieve a certain physiological effect in a subject. Alternatively, the methods and uses may be used in vitro to cleave a substrate of ACE2 in a sample, for example to detect AngI or AngII by cleaving said AngI or AngII with the ACE2 polypeptides of the invention. Optionally, the cleavage products are detected. In one embodiment, the sample is a plasma or serum sample. Metal ion-free ACE2 polypeptides in human plasma show the same enzymatic activity as zinc-containing or zinc-saturated ACE2 (see Example 3). It is believed that there are sufficient quantities of free zinc in human plasma to be taken up into the active site and reconstitute enzyme activity.

According to a fourth aspect of the present invention, there is provided a metal-ion substituted ACE2 polypeptide or a population of metal-ion substituted ACE2 polypeptides, wherein the active site is occupied by one or more transition metal ions, or post-transition metal ions, with the proviso that the active site is not occupied by $Zn^{2+}$. The metal ion is, in one embodiment, positively charged, in particular 2+ or 3+. In another embodiment, a transition element of the periodic table of elements is of groups 3 to 12 in periods 4, 5, 6 and 7, including Cr, Co, Ni, Mn, Cu, Fe, Mo, Ru, Rh, Pd, Ag and Cd, for example $Co^{2+}$, $Ni^{2+}$, $Mn^{2+}$, $Cu^{2+}$, $Fe^{3+}$, $Fe^{2+}$ and $Pb^{2+}$. In other embodiments, the transition element is a period 4 or 5 element. In a further embodiment, the transition metal is selected from $Co^{2+}$, $Ni^{2+}$ and $Pb^{2+}$. In a further embodiment, the metal ion is selected from $Fe^{3+}$, $Cu^{2+}$, and $Mn^{2+}$. In a further embodiment, the transition metal is selected from $Co^{2+}$ and $Ni^{2+}$. In another embodiment, the transition metal is selected from $Fe^{3+}$ and $Mn^{2+}$. Post-transition metals, also referred to as poor metals, are selected from Al, Ga, In, Sn, Tl, Pb, Bi and Po, e.g. $Al^{2+}$, $Al^{3+}$ and $Sn^{2+}$. In one embodiment, the post-transition metal is selected from aluminium and tin. For the avoidance of doubt, the metal-ion substituted ACE2 polypeptides may comprise any combination of metal ions from the transition metals and post-transition metals as described hereinabove.

The native zinc ion bound to the active site of ACE2 may be substituted by other metal ions while retaining catalytic activity. The metal ion is selected from a transition metal ion or post-transition metal ion as defined hereinabove. The metal-substituted ACE2 polypeptides may comprise any one of these metals or combinations thereof.

The metal-substituted ACE2 polypeptides may be provided in preparations or compositions wherein the ACE2 enzyme is substantially free of zinc. However small impurities of zinc may remain, and considered to be within the scope of the present invention.

Hence, in one embodiment, the native zinc is substantially completely replaced by another transition metal or post-transition metal ion as defined above. In another embodiment, the molar ratio of said metal ion:ACE2 is $\geq 0.10:1$, $\geq 0.15:1$, $\geq 0.20:1$, $\geq 0.25:1$, $\geq 0.30:1$, $\geq 0.35:1$, $\geq 0.40:1$, $\geq 0.45:1$, $\geq 0.50:1$, $\geq 0.55:1$, $\geq 0.60:1$, $\geq 0.65:1$, $\geq 0.75:1$, $\geq 0.80:1$, $\geq 0.85:1$, $\geq 0.90:1$, $\geq 0.92:1$, $\geq 0.95:1$, $\geq 0.98:1$, $\geq 0.99:1$ or about 1.00:1. In yet another embodiment, each individual ACE2 polypeptide contains one replacement metal ion. A preparation or composition of metal-substituted ACE2 polypeptides may comprise excess metal ions of any metal substitute or combinations thereof. A preparation or composition may further comprise additional metal ions in concentrations of at least 1.1 times, 1.3 times, 1.5 times, 1.8 times, 2 times, 2.5 times, 3 times, 3.5 times, 4 times, 4.5 times, 5 times, 7.5 times, 10 times, 15 times, 20 times, 25 times, 30 times, 40 times, 50 times or even 100 times the concentration of metal-substituted ACE2 polypeptides.

In a fourth aspect of the present invention, there is provided a population of mixed metal ACE2 polypeptides which polypeptides comprise a proportion of $Zn^{2+}$, and a proportion of one or more other transition metal ions or post-transition metal ions (which may be positively charged, in particular 2+ or 3+), in the active site. In one embodiment, the population of mixed metal ACE2 polypeptides comprise $Zn^{2+}$ and at least one metal ion selected from a transition elements selected from Cr, Co, Ni, Mn, Cu, Fe, Mo, Ru, Rh, Pd, Ag and Cd, for example $Co^{2+}$, $Ni^{2+}$, $Mn^{2+}$, $Cu^{2+}$, $Fe^{3+}$, $Fe^{2+}$ and $Pb^{2+}$. In other embodiments, the transition element is a period 4 or 5 element. In a further embodiment, the transition metal is selected from $Co^{2+}$, $Ni^{2+}$ and $Pb^{2+}$. In a further embodiment, the metal ion is selected from $Fe^{3+}$, $Cu^{2+}$, and $Mn^{2+}$. In a further embodiment, the transition metal is selected from $Co^{2+}$ and $Ni^{2+}$. In another embodiment, the transition metal is selected from $Fe^{3+}$ and $Mn^{2+}$. Post-transition metals are selected from Al, Ga, In, Sn, Tl, Pb, Bi and Po, e.g. $Al^{2+}$, $Al^{3+}$ and $Sn^{2+}$. In one embodiment, the post-transition metal is selected from aluminium and tin. For the avoidance of doubt, the mixed metal ACE2 polypeptides may comprise any combination of metal ions from the transition metal and post-transition metal, with or without zinc as described hereinabove.

The mixed metal ACE2 polypeptides are prepared from a zinc-depleted ACE2 polypeptide as described hereinabove. Hence, in one embodiment, the molar ratio of $Zn^{2+}$:ACE2 in the metal-substituted ACE2 polypeptide is $\leq 0.50:1$, $\leq 0.45:1$, $\leq 0.40:1$, $\leq 0.35:1$, $\leq 0.30:1$, $\leq 0.25:1$, $\leq 0.20:1$, $\leq 0.15:1$, $\leq 0.10:1$, $\leq 0.05:1$, $\leq 0.02:1$, or $\leq 0.01:1$. The $Zn^{2+}$:ACE2 ratio refers to zinc found in the zinc binding site of ACE2. This may be measured as described hereinabove.

In order to keep $Zn^{2+}$ from migrating to the binding site, a preparation or composition comprising a population of zinc-depleted ACE2 polypeptides of the invention also comprises little (according to the above ratios) or no free zinc. Free zinc levels (as well as zinc bound to the active site of ACE2) may be reduced in a particular preparation or composition by the addition of chelators also as described hereinabove.

The present invention further provides a method of producing metal-substituted ACE2 polypeptide or a mixed metal ACE2 polypeptide, comprising the steps of expressing an ACE2 polypeptide in a cell, isolating said ACE2 polypeptide and removing, or partially removing, $Zn^{2+}$ from said ACE2 polypeptide, preferably with a metal-chelating agent, to obtain either a zinc-free or zinc-depleted ACE2 polypeptide, and subsequently contacting said polypeptide with transition metal ions or post-transition metal ions. The ACE2 polypeptides may be expressed in the presence or absence of zinc. However, in most cellular systems zinc ions may be present and therefore the expressed ACE2 protein usually contains zinc in the active site. This bound zinc may subsequently be removed e.g. by using a metal-chelating agent, such as EDTA, EGTA, 8-hydroxyquinoline, phenanthroline and/or dimercaprol, or by using ion-exchange chromatography. In another embodiment, the metal-chelating agent is used in excess, e.g. in concentrations of at least 2 times, 5 times, 10 times, 25 times, 50 times, 75 times, 100 times, 200 times, 300 times, 400 times, 500 times, 600 times, 700 times, 800 times, 900 times, 1000 times the total concentration of zinc in the preparation or composition, i.e. the zinc concentration in the solution and in the active site. After full or partial removal of zinc (and optionally of the metal-chelating agent) a transition metal ion or post-transition metal ion is contacted with the zinc-depleted or zinc-free ACE2 polypeptide, which is readily taken up into the zinc binding site of the enzyme.

The enzymatic activity of metal-substituted and mixed-metal ACE2 polypeptides is different for each of the metal substitutes. Some metal ions, at low concentrations, show identical activities compared to native zinc-containing ACE2 polypeptides, but are shown to have reduced catalytic activity at higher concentrations. Others metal ions achieve similar catalytic activity to native zinc-containing ACE2 polypeptides only at higher concentrations (see Example 4). Hence, the specific catalytic activity of a metal-substituted or mixed-metal ACE2 polypeptide may be fine-tuned by choosing between different metal ions and their given concentration. It is within the capability of one skilled in the art to screen and select suitable metal ions and concentrations for any particular application.

Hence, there is also provided the use of a transition metal ion or a post-transition metal ion (as defined above) for modulating the catalytic activity of a population of ACE2 polypeptide, comprising substituting a proportion of zinc ions for said metal ion. There is further provided a method for modulating the catalytic activity of a population of ACE2 polypeptide, comprising substituting a proportion of zinc ions for a transition metal ion or a post-transition metal ion (as defined above). There is yet further provided the use of a metal-substituted ACE2 polypeptide or a population of mixed-metal ACE2 polypeptides to cleave an ACE2 substrate in a solution. There is also provided a method of cleaving an ACE2 substrate comprising contacting said ACE2 substrate with a metal-substituted ACE2 or a population of mixed-metal ACE2 polypeptide(s) in a solution.

Examples of ACE2 substrates include, but are not limited to, Apelin, Pro-Dynorphin, Des-Arg-Bradykinin, bradykinin, angiotensin I (Ang I, which is cleaved to angiotensin 1-9 [Ang1-9]), angiotensin II (Ang II, which is cleaved to angiotensin 1-7 [Ang1-7]) and others. Furthermore, a number of artificial substrates exists, such as those described in US2010/0261214 (see paragraph [0032], on page 3, incorporated herein by reference), e.g. Mca-Ala-Pro-Lys(Dnp)-OH (Mca: (7-methoxy coumarin-4-yl)acetyl). Artificial substrates may be labelled, e.g. comprise both a fluorophore and a quencher, such that upon cleavage an optical signal is generate. The methods and uses of zinc-depleted, zinc-free and/or metal ion-free ACE2 polypeptides to cleave ACE2 substrates may further comprise the step of detecting cleavage products.

The methods and uses of zinc-depleted, zinc-free and/or metal ion-free ACE2 polypeptides to cleave ACE2 substrates may be performed in vivo, for example for therapeutic uses or to achieve a certain physiological effect in a subject. Alternatively, the methods and uses may be used in vitro to cleave a substrate of ACE2 in a sample, for example to detect AngI or AngII by cleaving said AngI or AngII with the ACE2 polypeptides of the invention. Optionally, the cleavage products are detected. In one embodiment, the sample is a plasma or serum sample.

In a fifth aspect of the present invention, the zinc-depleted ACE2 polypeptides, zinc-free ACE2 polypeptides, metal-substituted ACE2 polypeptides and mixed-metal ACE2 polypeptides may be provided in form of a pharmaceutical composition. The following description of compositions, medical uses and methods of treatment are applicable to each of zinc-depleted ACE2 polypeptides, metal ion-free ACE2 polypeptides, metal-substituted ACE2 polypeptides and mixed-metal ACE2 polypeptides, which will hereinafter be referred to as "ACE2 polypeptide(s) of the invention".

There is thus provided a pharmaceutical composition comprising an ACE2 polypeptide of the invention and a pharmaceutically acceptable carrier or diluents. Such pharmaceutical compositions may further comprise pharmaceutically acceptable salts (and salts of the ACE2 polypeptides of the invention) and optionally additional buffers, tonicity adjusting agents, pharmaceutically acceptable vehicles, and/or stabilizers. Pharmaceutically acceptable carriers or diluents are used to improve the tolerability of the composition and allow better solubility and better bioavailability of the active ingredients. Examples include emulsifiers, thickeners, redox components, starch, alcohol solutions, polyethylene glycol or lipids. The choice of suitable pharmaceutical carriers or diluents depends greatly on how the composition is to be administered. Liquid or solid carriers or diluents may be used for oral administration; whereas liquid compositions are required for injections.

The pharmaceutical composition according to the invention may further comprise buffers or tonicity-adjusting agents. The pH of the composition may be adjusted to correspond to physiological pH by means of buffers, and fluctuations in pH may also be buffered. Buffers include, but are not limited to, for example a phosphate buffer or a MES (2-(N-morpholino)ethanesulfonic acid) buffer. In one embodiment, the pH of the pharmaceutical composition is between 4 and 10, such as between 5 and 9.5, such as between 6 and 9. Tonicity adjusting agents are used to adjust the osmolarity of the composition and may contain ionic substances, such as inorganic salts, e.g., NaCl, or nonionic substances, such as glycerol or carbohydrates.

The pharmaceutical composition according to the invention is suitably prepared for systemic, topical, oral or intranasal administration. These modes of administration of the pharmaceutical composition allow a rapid and uncomplicated uptake of active substance. For example, for oral administration, solid and/or liquid medications may be administered directly, or alternatively may be dissolved and/or diluted prior to administration. In one embodiment, the pharmaceutical compositions are liquid, in particular aqueous compositions.

The pharmaceutical composition according to the invention may be suitably prepared for intravenous, intra-arterial, intramuscular, intravascular, intraperitoneal or subcutaneous administration. For example, injections or transfusions may be used. Administration directly into the bloodstream has the advantage that the active substance(s) of the composition are distributed throughout the entire body for systemic therapy, and rapidly reach the target tissue(s). In one embodiment, the pharmaceutical composition is prepared for intravenous administration, and may be in liquid form.

The ACE2 polypeptides of the invention may be used in the treatment of various diseases as precedented in the art for zinc-comprising ACE2 polypeptides.

According to a sixth aspect of the present invention, there is provided an ACE2 polypeptide, or population of ACE2 polypeptides of the invention for use in therapy, such as for the treatment of various diseases and conditions. Also provided are methods of treatment of various diseases and conditions, comprising administering to a patient in need thereof an effective amount of an ACE2 polypeptide, or population of ACE2 polypeptides of the invention. The invention further provides the use of an ACE2 polypeptide, or population of ACE2 polypeptides of the invention in the manufacture of a medicament for the treatment of various diseases and conditions. The various diseases and conditions will be described in more detail as follows.

The ACE2 polypeptides, or populations of ACE2 polypeptides of the invention may be used to treat or prevent hypertension (including high blood pressure), congestive heart failure, chronic heart failure, acute heart failure, contractile heart failure, myocardial infarction, arteriosclerosis, kidney disease, renal failure and lung disease, such as Adult Respiratory Distress Syndrome (ARDS), Acute Lung Injury (ALI), chronic obstructive pulmonary disease (COPD), pulmonary hypertension, renal fibrosis, chronic renal failure, acute renal failure, chronic renal failure, acute kidney injury and multi-organ dysfunction syndrome (e.g. as disclosed in WO2004/000367, see page 7 line 23 to page 8, line 3 and page 21, line 3 to line 26, incorporated herein by reference). The ACE2 polypeptides, or populations of ACE2 polypeptides of the invention may be used to decrease blood pressure. Preferably, the treatment is of the heart or kidney or lung or blood vessels. The invention provides treatment of heart disease, lung disease and kidney disease, hypertension and multi-organ dysfunction syndrome by administration of the ACE2 polypeptides, or populations of ACE2 polypeptides of the invention. Lung diseases include, but are not limited to ARDS, ALI, COPD, pneumonia, asthma, chronic bronchitis, pulmonary emphysema, cystic fibrosis, interstitial lung disease, primary pulmonary hypertension, pulmonary embolism, pulmonary sarcoidosis, tuberculosis, lung cancers, artherosclerosis, polycystic kidney disease (PKD), oedema of the lung and, optionally, pulmonary hypertonia. Kidney diseases include, but are not limited to renal fibrosis, chronic renal failure, acute renal failure, chronic renal failure and acute kidney injury.

The present invention relates to the therapeutic treatment or prevention of an inflammation as disclosed in WO2009/076694, see page 4 and first paragraph of page 5, incorporated herein by reference. The inflammation is preferably a local inflammation of a tissue or organ and/or a systemic inflammation. Based on the general mechanism, it is possible to treat both chronic and acute inflammations. In particular, the inflammation may include, but is not limited to, rheumatism, sepsis, osteoarthritis, rheumatoid arthritis, systemic lupus erythematosus, scleroderma or mixed connective tissue disease. These conditions may be caused by mechanical or chemical cellular damage or tissue damage or wounds, infections, in particular pathogens such as viruses, bacteria, or fungi, by implants including organ implants and by medications. In one embodiment, the inflammation is caused by an infection.

The inflammation may also comprise an autoimmune disease. The disease may be, for example, an antiglomerular basal membrane disease, autoimmune diseases of the nervous system, systemic lupus erythematosus (SLE), Addison's disease, an antiphospholipid syndrome, an IgA glomerulonephritis, a Goodpasture syndrome, a Lambert-Eaton myasthenic syndrome, idiopathic purpura, an autoimmune thyroiditis, a rheumatoid arthritis, an insulin-dependent diabetes mellitus, an pemphigus, an autoimmune hemolytic anemia, a dermatitis herpetiformis Durhing, a membranous glomerulonephritis, a Graves disease, a sympathetic ophthalmia, autoimmune polyendocrinopathies, multiple sclerosis and/or Reiter's disease.

The present invention relates to the treatment of fibrosis, as e.g. disclosed in WO2009/086572 page 3, fourth paragraph to page 6, first paragraph, incorporated herein by reference. In one embodiment, the fibrosis is a local fibrosis of a tissue or organ. Such organ-specific fibroses include, but are not limited to, hepatic fibroses, pulmonary fibroses, connective tissue fibroses, in particular fibrosis of the muscle septa, renal fibrosis, and fibrosis of the skin, e.g., in combination with an inflammation-scleroderma. The fibrosis may be a fibrosis of an internal organ, e.g., the liver, kidneys, lungs, heart, stomach, intestines, pancreas, glands, muscles, cartilage, tendons, ligaments or joints. Cystic fibrosis or rheumatic fibrosis is a type of fibrosis. In another embodiment, the fibrosis occurs concurrently with inflammation, e.g. hepatitis (inflammatory liver disease). In another embodiment, the fibrosis is associated with organ transplantation.

The fibrosis is preferably attributed to an excessive deposit of the components of the extracellular matrix, in particular proteins such as collagen. Collagen is a structural protein of the connective tissue, in particular the extracellular matrix. The formation of collagen, in particular in combination with the SMA (smooth muscle actin) marker correlates directly with the progression of fibrosis. According to the invention, effective inhibition of deposition of collagen by ACE2 has been observed.

In addition, based on the general mechanism, the treatment of chronic fibrosis is also possible. In particular, the fibrosis may be caused by mechanical or chemical cell or tissue damage or wounds, cancer or tumors, infections, in particular pathogens such as viruses, bacteria or fungi, by implants, including organ implants as well as medications. Infections may be organ-specific, for example, such as hepatitis virus infection, in particular due to HCV. Other preferably fibrotic diseases, which may be treated with the ACE2 polypeptides of the present invention, include, for example, primary or secondary fibroses, in particular fibroses caused by an autoimmune response, Ormond's disease (retroperitoneal fibrosis).

The present invention relates to the treatment of liver disease as e.g. disclosed in WO2009/086572. In some embodiments, the fibrosis or liver disease occurs concurrently with inflammation, e.g. hepatitis (inflammatory liver disease).

The present invention relates to the treatment of tumour diseases and cancer e.g. as disclosed in WO2009/124330, see page 6 to page 9, fifth paragraph, incorporated herein by reference. Preferably the tumour diseases is selected from a tumour disease of the reproductive tract, in particular ovarian cancer, testicular cancer, prostate cancer or breast cancer, tumour diseases of the digestive tract, in particular stomach cancer, intestinal cancer, rectum carcinoma, pancreatic cancer, esophagus cancer and liver cancer, kidney cancer, lung cancer, melanomas or neuroblastomas.

In another embodiment, the present invention relates to the treatment of diabetes, including diabetic nephropathy.

The present invention is further illustrated by the following figures and examples without being limited to these specific embodiments of the invention.

EXAMPLES

Example 1 ACE2 Standard

An ACE2 formulation was obtained as described previously (WO 2008/151347, see example 1) used with an equimolar zinc/protein ratio. This ratio of 1:1 was confirmed by quantitative amino-acid analysis and ICP-MS analysis of zinc content. ICP analysis was carried out as follows: Prior to analysis, the samples were diluted with $HNO_3$ (supra pure, 1:100 v/v) and acidified (which resulted in a slight turbidity, but without influencing the results of the measurement). The zinc content was determined by inductively coupled mass spectrometry according to ÖNORM EN ISO 17294-2.

This material was used as the standard for fully enzymatically active ACE2. Hence, the activity is set to 100% for all further comparative studies investigating the influence of zinc, or other metals on enzymatic activity.

Example 2 Depletion of Zinc 2.0 mg ACE2 (prepared, for example as described in Example 1; 400 µl), formulated in 100 mM Glycine Buffer pH: 7.5 containing 150 mM NaCl and 50 µM $ZnCl_2$ were mixed with 100 µl 0.5 M EDTA, pH 8.0 to obtain a final concentration of 100 mM EDTA. The total zinc concentration in the sample is about 100 µM. This gives a molar ratio of zinc to EDTA of 1:1000 (i.e. one thousand-fold excess of EDTA). The solution was gently mixed and incubated for 14 h at room temperature.

Removal of EDTA was performed by buffer exchange using a Vivaspin concentrator device, by adding 1 ml 50 mM MES-Buffer pH 6.5 containing 300 mM NaCl. This was repeated twice more.

The final volume was 190 µl, and the ACE2 concentration in this sample was 8.2 mg/ml measured by its absorbance at 280 nm, and calculated by using an extinction coefficient of 163,680 l/mol×cm.

Figure 1:
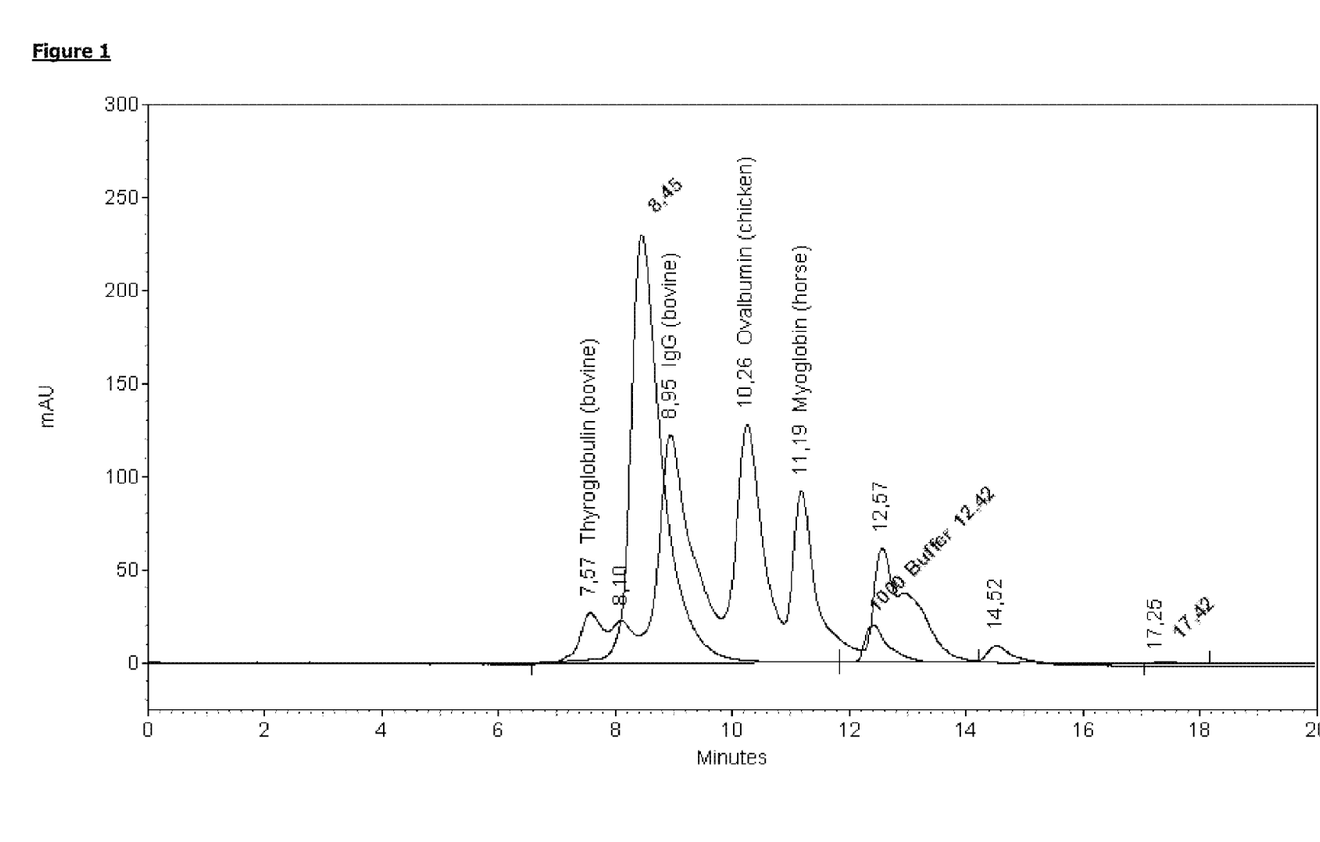
FIG. 1 shows an SEC-HPLC analysis of Zn-free dialyzed ACE2 (curve with one major peak at 8.4 min retention time), compared to a molecular weight reference standard (curve with multiple peaks).

Zinc-depleted ACE2 was analyzed by size exclusion chromatography as shown in FIG. 1. Molecular weight was determined by direct comparison to a GF-standard (Thyroglobulin, IgG, Ovalbumin and Myoglobin) and found to be 270640 Da. ACE2 eluted as single peak at the retention time of 8.4 minutes. Signals after 12 min retention are due to small buffer components. This study confirms the integrity of the enzyme preparation because ACE2 eluted as a single peak and accordingly, no aggregation or fragmentation of the protein has occurred during the removal of zinc. Interestingly, a zinc-free ACE2 preparation is stable and does not aggregate or disintegrate.

Example 3 Zinc Dependency of ACE2 Activity

Figure 2:
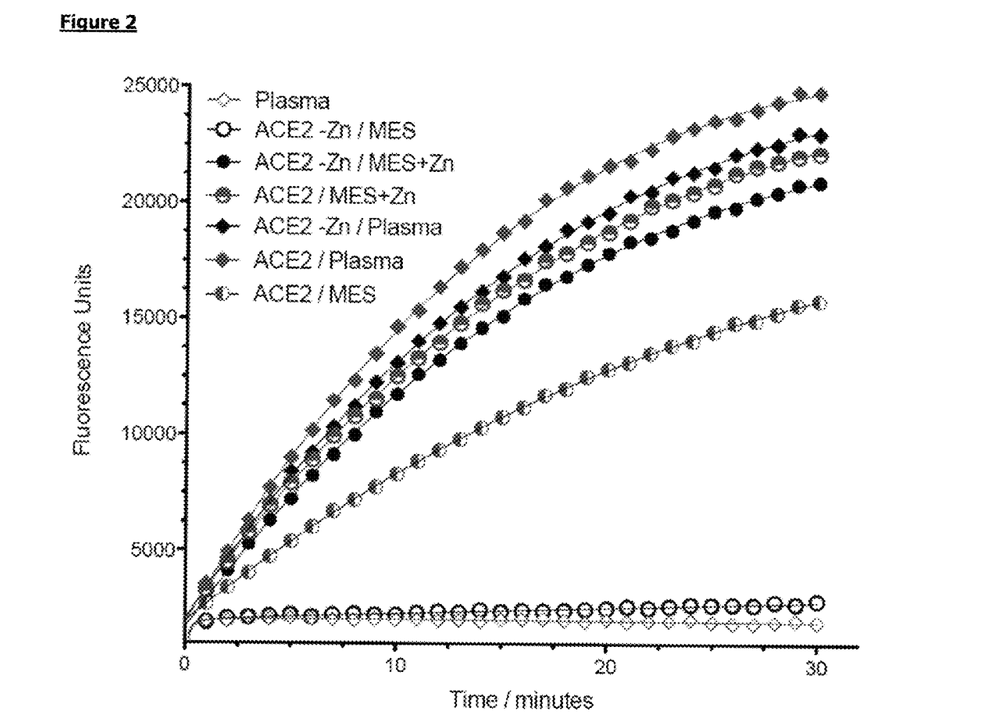
FIG. 2 shows ACE2 activity measured by detection of a fluorescent cleavage product in different formulations.

The enzymatic activity of ACE2 was investigated in a reaction buffer with and without addition of zinc and also in human heparin plasma to mimic the situation after systemic administration. Respective controls were the same buffers without zinc. A fluorescently labelled ACE2 substrate, Mca-Ala-Pro-Lys-DNP was used to quantify enzymatic activity. The DNP (di-nitro-phenyl) moiety quenches the Mca (Methoxy-cumarin-acetic-acid) fluorescence of the native peptide, but, upon cleavage by ACE2, a fluorescent signal becomes detectable. After incubation for about 30 minutes all samples were diluted with $H_2O$ in a ratio of 1:10. Finally, 50 µl of each sample were mixed with 50 µl of Mca-Ala-Pro-Lys-DNP, (1:5 pre-dilution with MES-NaCl Buffer) and immediately measured at 430 nm as emission wavelength, and 320 nm as excitation wavelength. Fluorescence-time curves were recorded and initial slopes were used to quantify respective ACE2 activities. Results are displayed in FIG. 2. The measured time-dependent relative fluorescence units (RFU's) were plotted for each sample. Curves were fitted with a second order polynomial curve $y=B0+B1t+B2t2$ where B1 is the initial slope of respective curves at t=0. B1 values are shown in Table 1 and correspond to the maximum cleavage activity.

TABLE 1

| ACE2 activity analysis | | |
|---|---|---|
| Sample | Description | $B_1$ FU/min ± std |
| ACE2*/MES + Zn | ACE2* 10 µg/ml in 50 mM MES + $ZnCl_2$(0.5 mg/ml) | 1139 ± 25 |
| ACE2*/Plasma | ACE2* 10 µg/ml in Human Plasma | 1254 ± 12 |
| ACE2*/MES | ACE2* 10 µg/ml in 50 mM MES | 25 ± 4 |
| ACE2/MES + Zn | ACE2 10 µg/ml in 50 mM MES + $ZnCl_2$(0.5 mg/ml) | 1176 ± 27 |
| ACE2/Plasma | ACE2 10 µg/ml in Human Plasma | 1436 ± 18 |
| ACE2/MES | ACE2 10 µg/ml in 50 mM MES | 708 ± 8 |
| Plasma | Human Plasma alone | 4 ± 4 |

ACE2* = ACE2 lacking $Zn^{2+}$

Human plasma alone as well as Zn-depleted ACE2 in MES buffer did not cleave the fluorescently labelled substrate to any significant degree. Maximal activities were 4±4 and 25±4 FU/min, respectively. This concludes that human plasma does not show an important intrinsic ACE2 activity and that Zn-depleted ACE2 loses its enzymatic activity. In contrast to this observation, $Zn^{2+}$ containing ACE2 samples show a strong activity in MES buffer (708±8 FU/min). This activity is nearly doubled in human plasma (1436±18 FU/min). Addition of 0.5 mg/ml $Zn^{2+}$ to MES buffer increases ACE2 activity up to 1176±27 FU/min, and almost completely returns activity to Zn-depleted ACE2 (1139±25 FU/min).

Interestingly, zinc-depleted ACE2 becomes fully enzymatically active in human plasma (1254±12 FU/min) without any extraneous addition of $Zn^{2+}$. This activity is nearly identical when compared to the one of Zn-containing ACE2.

Example 4 Metal-Ion Dependency of ACE2 Activity

The enzymatic activity of ACE2 was also investigated in a different set of reaction buffers, which were supplemented with different metal ions in order to replace $Zn^{2+}$ by other positively charges metal ions. The same fluorescently labelled ACE2 substrate Mca-Ala-Pro-Lys-DNP as described before was used to quantify resulting enzymatic activity. Therefore depleted ACE2 was prediluted with MES-NaCl buffer to a concentration of 20 µg/ml. Serial dilutions containing 10, 5, 2.5, 1.25, 0.63, 0.31, 0.15 and 0.063 µg/ml ACE2 were generated by diluting with 50 µM $Zn^{2+}$, 25 µM $Co^{2+}$, 50 µM $Ni^{2+}$, 50 µM $Fe^{2+}$, 25 µM $Fe^{3+}$, 50 µM $Pb^{2+}$, 50 µM $Mg^{2+}$, 50 µM $Mn^{2+}$ and 50 µM $Cu^{2+}$ solution and incubated for 30 min. 50 µl of each sample was mixed with 50 µl of substrate Mca-Ala-Pro-Lys-DNP, (1:5 predilution with MES-NaCl Buffer) and immediately measured at 430 nm as emission wavelength, and 320 nm as excitation wavelength. Fluorescence-time curves were recorded and initial slopes were used to quantify respective ACE2 activities. Time-dependent relative fluorescence units (RFU's) were plotted for each sample. Curves were fitted with a second order polynomial curve $y=B0+B1t+B2t2$ where B1 is the initial slope of respective curves at t=0. B1 correspond to maximal activities and values are shown in Table 2.

TABLE 2

Metal Ion dependent ACE2 activity
B1 FU/min

| | ACE2 conc. µg/ml | | | | |
|---|---|---|---|---|---|
| | 0.625 | 1.25 | 2.5 | 5.0 | 10.0 |
| $Zn^{2+}$ | 54 | 122 | 283 | 608 | 1465 |
| $Co^{2+}$ | 38 | 84 | 211 | 478 | 1139 |
| $Ni^{2+}$ | 36 | 55 | 125 | 287 | 1010 |
| $Pb^{2+}$ | 6 | 27 | 56 | 186 | 1007 |
| $Mn^{2+}$ | 54 | 124 | 245 | 306 | 181 |
| $Cu^{2+}$ | 12 | 6 | 23 | 61 | 136 |
| $Fe^{3+}$ | 37 | 117 | 204 | 0 | 3 |
| $Fe^{2+}$ | 13 | 4 | 10 | 53 | 190 |
| $Mg^{2+}$ | 0 | 6 | 0 | 0 | 0 |
| Depleted | 0 | 0 | 0 | 8 | 0 |

Zinc depleted ACE2 was enzymatically inactive. At a concentration of 10 µg/ml ACE2 and 50 µM $Zn^{2+}$ (corresponding to a molar ratio of 1:250) shows the highest specific ACE2 activity and was set therefore to 100%. Comparable activities were reached with $Co^{2+}$ (78%) and $Ni^{2+}$ as well as $Pb^{2+}$ (both about 69%).

All other investigated metal ions had significantly lower activity at a concentration of 10 µg/ml ACE2: Activity of $Fe^{2+}$ and $Mn^{2+}$ supplemented ACE2 was in the range of 13% and $Cu^{2+}$ at 9%. $Fe^{3+}$, $Mg^{2+}$ as well as metal ion depleted ACE2 were practically inactive.

Interestingly, $Fe^{3+}$ and $Mn^{2+}$, which both were at 10 µg/ml significantly less active than $Zn^{2+}$ containing ACE2, showed at lower ACE2 concentrations of 0.625 and 1.25 µg/ml practically the same specific activity when compared to $Zn^{2+}$.

Figure 3:
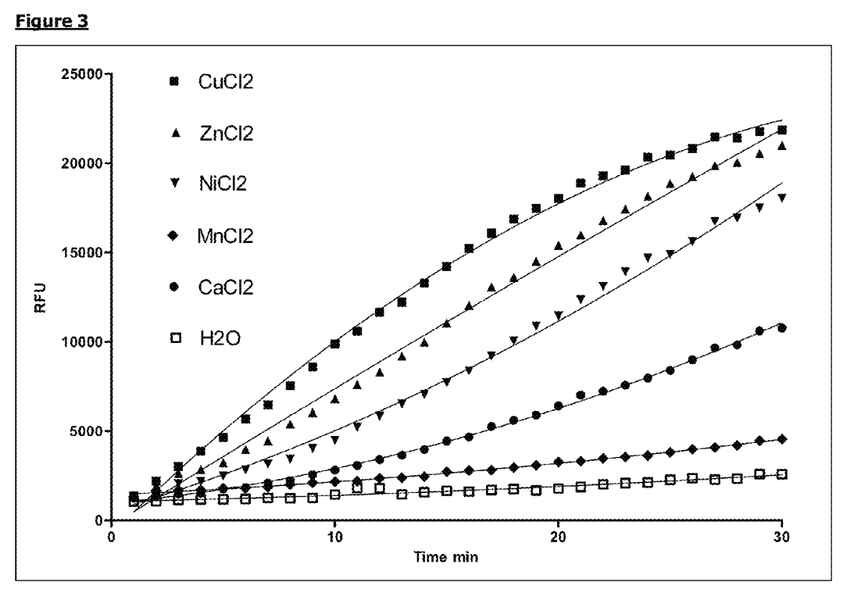
FIG. 3 shows measured relative fluorescence units (RFUs) plotted per cycle (1 min) for rACE2 samples, 1 μM metal ion concentration and 15 min incubation.
Figure 4:
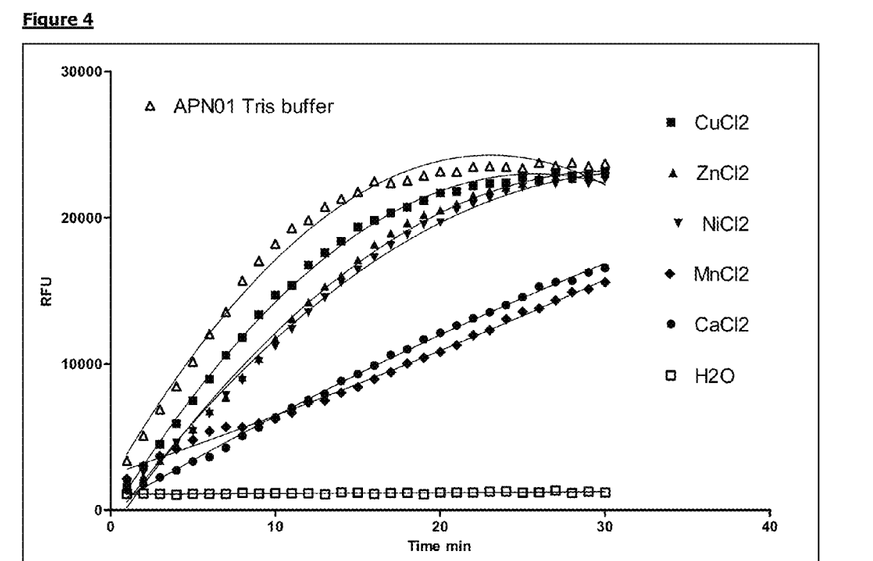
FIG. 4 shows measured relative fluorescence units (RFUs) plotted per cycle (1 min) for rACE2 samples, 1 μM metal ion concentration and 80 min incubation.
Figure 5:
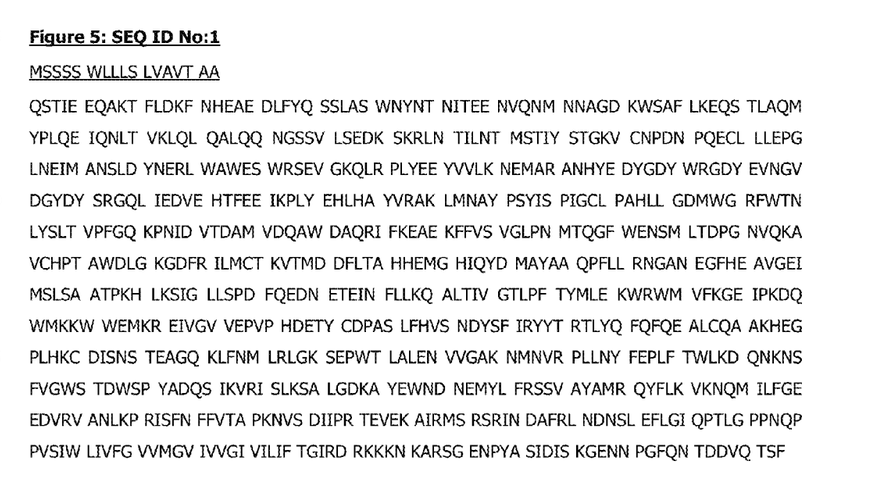
FIG. 5 shows the full-length amino acid sequence of human ACE2 (SEQ ID No: 1). Amino acids 1-17 are the signal sequence, 18-740 form the extracellular domain, 741-761 form the transmembrane domain and 762-805 form the cytoplasmic domain.

Example 5 Metal-Ion Dependency of ACE2 Activity rhACE2 stock solutions (as prepared above in Examples 1 and 2) were diluted to a 1 µM solution with cell culture grade water. Metal ion solutions of $CuCl_2$, $ZnCl_2$, $NiCl_2$, $MnCl_2$ and $CaCl_2$ with a concentration of 1 µM were prepared out of a 10 mM stock solution. To achieve an equimolar ratio of enzyme to soluble metal ion, incubation with 1 µM metal ion solutions were conducted for 15 min and 80 min. For enzymatic activity testing, samples were diluted 1:10 with the according metal ion solution and further diluted 1:10 with MES-NaCl buffer. Activity testing was conducted by adding 50 µl of 200 µM substrate solution in activity buffer with 0.5 µM EDTA supplement to 50 µl sample dilution and immediately measured by a fluorescence detector, Anthos Zenyth 3100, Ser. No. 26001070 with wavelengths filter of 320 nm for excitation and 430 nm for emission. The measured relative fluorescence units (RFUs) were plotted per cycle (1 min) for each rACE2 sample (see FIGS. 3 and 4). To calculate slope values each curve were fitted by second order polynomial curve ($Y=B0+B1*X+B2*X^2$). B1 values are shown below.

TABLE 3

1 µM metal ion concentration, 15 min incubation:

| | Metal ion conc. (incubation, 15 min) | | | | | | |
|---|---|---|---|---|---|---|---|
| Cycle 1-30 | 1 µM $CuCl_2$ | 1 µM $ZnCl_2$ | 1 µM $NiCl_2$ | 1 µM $MnCl_2$ | 1 µM $CaCl_2$ | 1 µM $H_2O$ | 1 µM APN01 Tris Buffer |
| B1 | 1228 | 779.8 | 370.2 | 57.57 | 123.2 | 27.62 | n.d. |
| B1 (%) | 157 | 100 | 47 | 7 | 16 | 4 | |
| Std. Error | | | | | | | |
| B1 | 58.56 | 65.16 | 105.1 | 6.343 | 28.82 | 9.651 | n.d. |

TABLE 4

1 µM metal ion concentration, 80 min incubation:

| | Metal ion conc. (80 min. incubation) | | | | | | |
|---|---|---|---|---|---|---|---|
| Cycle 1-30 | 1 µM $CuCl_2$ | 1 µM $ZnCl_2$ | 1 µM $NiCl_2$ | 1 µM $MnCl_2$ | 1 µM $CaCl_2$ | 1 µM $H_2O$ | 1 µM APN01 Tris Buffer |
| B1 | 1819 | 1619 | 1487 | 383.6 | 653.9 | 4.176 | 1937 |
| B1 (%) | 112 | 100 | 92 | 24 | 40 | 0 | |
| Std. Error | | | | | | | |
| B1 | 30.91 | 30.49 | 31.93 | 17.03 | 30.63 | 4.288 | 48.55 |

As negative control, $Zn^{2+}$ depleted ACE2 was enzymatically inactive. Specific activity of the $Zn^{2+}$ incubated sample was set to 100%. After 80 min incubation, comparable activities were reached with $Cu^{2+}$ (112%) and $Ni^{2+}$ (92%). Incubation with $Mn^{2+}$ or $Ca^{2+}$ ions resulted in significantly lower activity (up to 40%).

The invention claimed is:

1. A pharmaceutical composition comprising a population of angiotensin converting enzyme 2 (ACE2) polypeptides having depleted levels of $Zn^{2+}$ in the active sites and a pharmaceutically acceptable carrier or excipient.

2. The pharmaceutical composition according to claim 1, wherein the ratio of $Zn^{2+}$:ACE2 polypeptides is less than 1:1, preferably ≤0.99:1, ≤0.98:1, ≤0.95:1, ≤0.92:1 or ≤0.90:1.

3. The pharmaceutical composition according to claim 2, wherein the ratio of $Zn^{2+}$:ACE2 polypeptides is ≤0.50:1, ≤0.45:1, ≤0.40:1, ≤0.35:1, ≤0.30:1, ≤0.25:1, ≤0.20:1, ≤0.15:1, ≤0.10:1, ≤0.05:1, ≤0.02:1, or ≤0.01:1.

4. The pharmaceutical composition according to claim 1, wherein the ACE2 polypeptides are human ACE2 polypeptides.

5. The pharmaceutical composition according to claim 4, wherein the amino acid sequences of the ACE2 polypeptides consist of amino acids 1 to 740 of SEQ ID NO: 1, or amino acids 18 to 740 of SEQ ID No: 1, or amino acids 18 to 615 of SEQ ID NO: 1.

6. The pharmaceutical composition according to claim 4, wherein the ACE2 polypeptides are present in dimeric form.

7. The pharmaceutical composition according to claim 1, wherein the active sites have no detectable levels of any metal ion.

8. The pharmaceutical composition according to claim 1, wherein the composition comprises a molar ratio of total zinc or other metal ion to ACE2 of less than 1:1, ≤0.95:1, ≤0.50:1, ≤0.45:1, ≤0.40:1, ≤0.35:1, ≤0.30:1, ≤0.25:1, ≤0.20:1, ≤0.15:1, ≤0.10:1, ≤0.05:1, ≤0.02:1, or ≤0.01:1.

9. The pharmaceutical composition according to claim 1, wherein the composition comprises metal chelators in a molar excess of 10 to 1000 as compared to the molar amount of zinc in the composition.

10. The pharmaceutical composition as defined in claim 1 for use in treating and preventing a human disease.

11. The pharmaceutical composition as defined in claim 1 for use in the treatment or prevention of a disease selected from hypertension (including high blood pressure), congestive heart failure, chronic heart failure, acute heart failure, contractile heart failure, myocardial infarction, arteriosclerosis, kidney failure, renal failure and lung disease, such as Adult Respiratory Distress Syndrome (ARDS), Acute Lung Injury (ALI), chronic obstructive pulmonary disease (COPD), pulmonary hypertension, renal fibrosis, chronic renal failure, acute renal failure, chronic renal failure, acute kidney injury and multi-organ dysfunction syndrome.

* * * * *

```
                         SEQUENCE LISTING

<160> NUMBER OF SEQ ID NOS: 1

<210> SEQ ID NO 1
<211> LENGTH: 805
<212> TYPE: PRT
<213> ORGANISM: Human

<400> SEQUENCE: 1

Met Ser Ser Ser Ser Trp Leu Leu Leu Ser Leu Val Ala Val Thr Ala
 1               5                  10                  15

Ala Gln Ser Thr Ile Glu Glu Gln Ala Lys Thr Phe Leu Asp Lys Phe
             20                  25                  30

Asn His Glu Ala Glu Asp Leu Phe Tyr Gln Ser Ser Leu Ala Ser Trp
         35                  40                  45

Asn Tyr Asn Thr Asn Ile Thr Glu Glu Asn Val Gln Asn Met Asn Asn
     50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
```

```
                340             345             350
Lys Gly Asp Phe Arg Ile Leu Met Cys Thr Lys Val Thr Met Asp Asp
            355             360             365
Phe Leu Thr Ala His His Glu Met Gly His Ile Gln Tyr Asp Met Ala
        370             375             380
Tyr Ala Ala Gln Pro Phe Leu Arg Asn Gly Ala Asn Glu Gly Phe
385             390             395             400
His Glu Ala Val Gly Glu Ile Met Ser Leu Ser Ala Ala Thr Pro Lys
                405             410             415
His Leu Lys Ser Ile Gly Leu Leu Ser Pro Asp Phe Gln Glu Asp Asn
            420             425             430
Glu Thr Glu Ile Asn Phe Leu Leu Lys Gln Ala Leu Thr Ile Val Gly
        435             440             445
Thr Leu Pro Phe Thr Tyr Met Leu Glu Lys Trp Arg Trp Met Val Phe
    450             455             460
Lys Gly Glu Ile Pro Lys Asp Gln Trp Met Lys Lys Trp Trp Glu Met
465             470             475             480
Lys Arg Glu Ile Val Gly Val Val Glu Pro Val Pro His Asp Glu Thr
                485             490             495
Tyr Cys Asp Pro Ala Ser Leu Phe His Val Ser Asn Asp Tyr Ser Phe
            500             505             510
Ile Arg Tyr Tyr Thr Arg Thr Leu Tyr Gln Phe Gln Phe Gln Glu Ala
        515             520             525
Leu Cys Gln Ala Ala Lys His Glu Gly Pro Leu His Lys Cys Asp Ile
    530             535             540
Ser Asn Ser Thr Glu Ala Gly Gln Lys Leu Phe Asn Met Leu Arg Leu
545             550             555             560
Gly Lys Ser Glu Pro Trp Thr Leu Ala Leu Glu Asn Val Val Gly Ala
                565             570             575
Lys Asn Met Asn Val Arg Pro Leu Leu Asn Tyr Phe Glu Pro Leu Phe
            580             585             590
Thr Trp Leu Lys Asp Gln Asn Lys Asn Ser Phe Val Gly Trp Ser Thr
        595             600             605
Asp Trp Ser Pro Tyr Ala Asp Gln Ser Ile Lys Val Arg Ile Ser Leu
    610             615             620
Lys Ser Ala Leu Gly Asp Lys Ala Tyr Glu Trp Asn Asp Asn Glu Met
625             630             635             640
Tyr Leu Phe Arg Ser Ser Val Ala Tyr Ala Met Arg Gln Tyr Phe Leu
                645             650             655
Lys Val Lys Asn Gln Met Ile Leu Phe Gly Glu Asp Val Arg Val
            660             665             670
Ala Asn Leu Lys Pro Arg Ile Ser Phe Asn Phe Val Thr Ala Pro
        675             680             685
Lys Asn Val Ser Asp Ile Ile Pro Arg Thr Glu Val Glu Lys Ala Ile
    690             695             700
Arg Met Ser Arg Ser Arg Ile Asn Asp Ala Phe Arg Leu Asn Asp Asn
705             710             715             720
Ser Leu Glu Phe Leu Gly Ile Gln Pro Thr Leu Gly Pro Pro Asn Gln
                725             730             735
Pro Pro Val Ser Ile Trp Leu Ile Val Phe Gly Val Val Met Gly Val
            740             745             750
Ile Val Val Gly Ile Val Ile Leu Ile Phe Thr Gly Ile Arg Asp Arg
        755             760             765
```

-continued

```
Lys Lys Lys Asn Lys Ala Arg Ser Gly Glu Asn Pro Tyr Ala Ser Ile
    770             775                 780

Asp Ile Ser Lys Gly Glu Asn Asn Pro Gly Phe Gln Asn Thr Asp Asp
785             790              795                 800

Val Gln Thr Ser Phe
                805
```